US007070569B2

(12) United States Patent
Heinonen et al.

(10) Patent No.: US 7,070,569 B2
(45) Date of Patent: Jul. 4, 2006

(54) NON-INVASIVE DETERMINATION OF CONDITIONS IN THE CIRCULATORY SYSTEM OF A SUBJECT

(75) Inventors: Erkki Heinonen, Helsinki (FI); Jan Ekstrom, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 269 days.

(21) Appl. No.: 10/091,169

(22) Filed: Mar. 4, 2002

(65) Prior Publication Data

US 2002/0169385 A1 Nov. 14, 2002

(30) Foreign Application Priority Data

Mar. 5, 2001 (EP) .................................. 01301955

(51) Int. Cl.
*A61B 5/08* (2006.01)
*A61B 5/02* (2006.01)

(52) U.S. Cl. ...................... 600/532; 600/529; 600/484; 600/500

(58) Field of Classification Search ........ 600/531–533, 600/538, 529, 481, 483–486, 490–503

See application file for complete search history.

(56) References Cited

U.S. PATENT DOCUMENTS

| | | | | |
|---|---|---|---|---|
| 4,204,545 A | * | 5/1980 | Yamakoshi | ................. 600/506 |
| 4,608,995 A | | 9/1986 | Linnarsson et al. | |
| 4,718,428 A | * | 1/1988 | Russell | ....................... 600/492 |
| 4,821,732 A | * | 4/1989 | Lippes | ........................ 600/363 |
| 5,088,332 A | | 2/1992 | Meriläinen et al. | |

(Continued)

FOREIGN PATENT DOCUMENTS

WO 98/26710 6/1998

(Continued)

OTHER PUBLICATIONS

*A Deep Breath Method for Noninvasive Estimation of Cardiopulmonary Parameters*, Richard R. Mitchell, International Journal of Clinical Monitoring and Computing 5: 53-64, 1988.

(Continued)

*Primary Examiner*—Robert L. Nasser
*Assistant Examiner*—Navin Natnithithadha
(74) *Attorney, Agent, or Firm*—Andrus, Sceales, Starke & Sawall, LLP

(57) ABSTRACT

A method for non-invasively determining functional cardiac output (FCO) and/or venous blood $CO_2$ partial pressure ($PvCO_2$). The amount of $CO_2$ ($VCO_2^N$) released from the blood and end capillary blood $CO_2$ content ($CcCO_2^N$) are determined from measurements from exhaled breathing gases. The $CO_2$ content of the breathing gases inhaled by the subject is increased and values for $VCO_2^R$ and $CcCO_2^R$ are obtained. A regression analysis is performed using the obtained $VCO_2^N$, $VO_2^R$, $CcCO_2^N$, and $CcCO_2^R$ values. The regression line is extrapolated to obtain a value for $CcCO_2$ when ($VCO_2$) is zero so that $CvCO_2$ becomes known. The $CvCO_2$ thus determined can be inserted in a non-differential form in the Fick equation, along with $VCO_2$ and $CcCO_2$ values from normal breathing, to determine FCO. To determine $PvCO_2$, $CvCO_2$ is altered in accordance with the amount of oxygen in the venous blood, to correctly indicate $PvCO_2$. The continuing validity of the FCO measurement can be examined on a breath-by-breath basis by noting changes in an indicator variable, such as $VCO_2$ or end tidal $CO_2$ amounts.

63 Claims, 5 Drawing Sheets

U.S. PATENT DOCUMENTS

| | | | |
|---|---|---|---|
| 5,197,481 A | 3/1993 | Fisher | |
| 5,285,793 A * | 2/1994 | Slovut et al. | 600/519 |
| 5,485,848 A * | 1/1996 | Jackson et al. | 600/485 |
| 5,533,511 A * | 7/1996 | Kaspari et al. | 600/485 |
| 5,836,300 A | 11/1998 | Mault | |
| 5,876,348 A * | 3/1999 | Sugo et al. | 600/490 |
| 5,918,596 A | 7/1999 | Heinonen | |
| 6,042,550 A | 3/2000 | Haryadi et al. | |
| 6,102,868 A | 8/2000 | Banner et al. | |
| 6,131,572 A | 10/2000 | Heinonen | |
| 6,200,271 B1 * | 3/2001 | Kuck et al. | 600/532 |
| 6,210,342 B1 * | 4/2001 | Kuck et al. | 600/504 |
| 6,217,524 B1 | 4/2001 | Orr et al. | |
| 6,227,196 B1 | 5/2001 | Jaffe et al. | |
| 6,238,351 B1 | 5/2001 | Orr et al. | |
| 6,306,098 B1 | 10/2001 | Orr et al. | |
| 6,371,921 B1 * | 4/2002 | Caro et al. | 600/485 |
| 6,540,689 B1 | 4/2003 | Orr et al. | |
| 2001/0029339 A1 | 10/2001 | Orr et al. | |
| 2001/0031928 A1 | 10/2001 | Orr et al. | |

FOREIGN PATENT DOCUMENTS

| | | |
|---|---|---|
| WO | 99/25244 | 5/1999 |
| WO | 00/42908 | 7/2000 |
| WO | 01/62148 | 8/2001 |

OTHER PUBLICATIONS

*A New Method for Noninvasive Bedside Determination of Pulmonary Blood Flow*, A. Gedeon et al., Medical & Biological Engineering & Computing, 1980, vol. 18, 411-418.

*Nunn's Applied Respiratory Physiology*, J. F. Nunn, published by Butterworths, pp. 224-225.

* cited by examiner

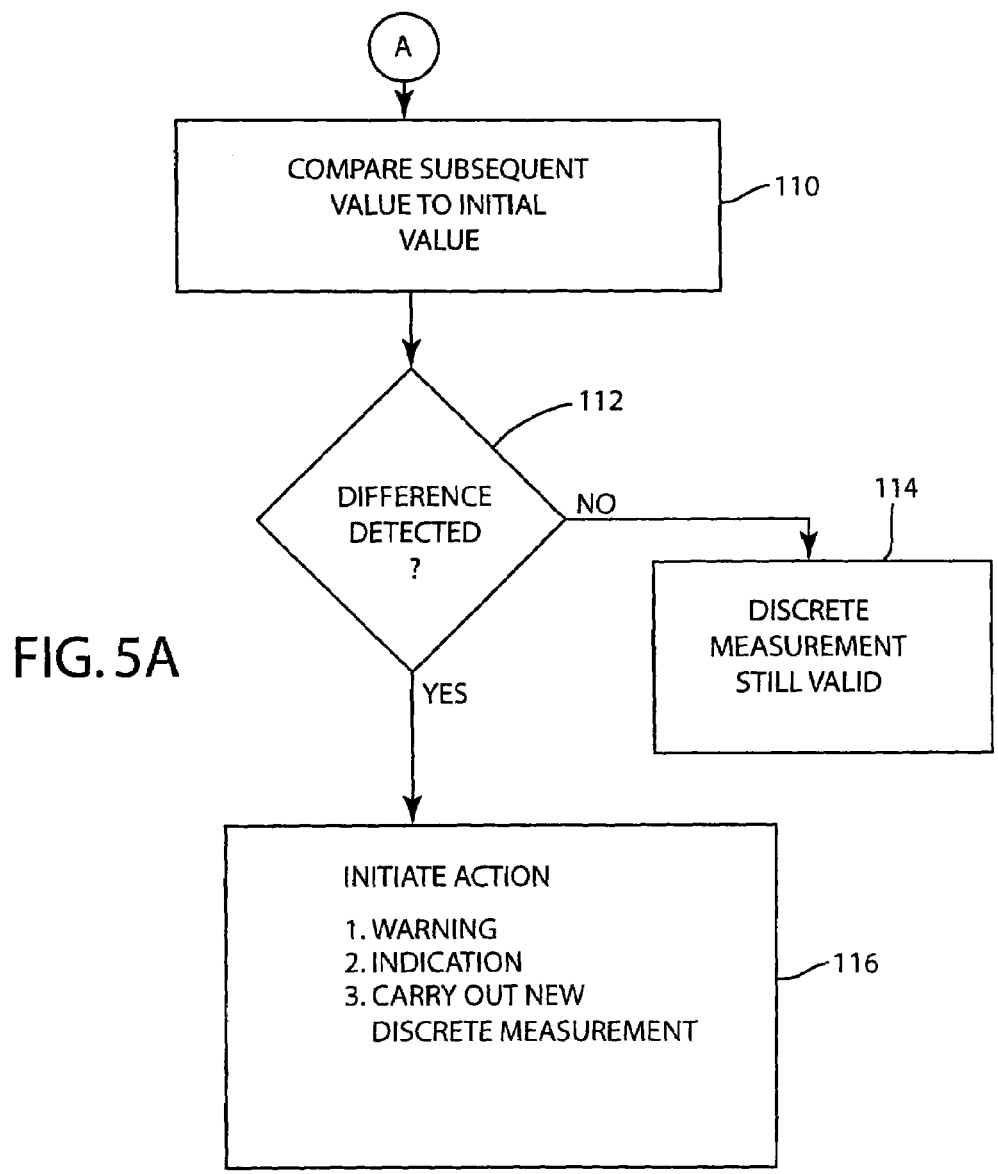

NON-INVASIVE DETERMINATION OF CONDITIONS IN THE CIRCULATORY SYSTEM OF A SUBJECT

CROSS REFERENCE TO RELATED APPLICATIONS

The present application claims the priority of European Patent Application 01 30 1955.9, filed Mar. 5, 2001.

BACKGROUND OF THE INVENTION

The present invention relates to improved methods for non-invasively determining a condition in the circulatory system of a subject. More particularly, the present invention is directed to non-invasively determining the functional cardiac output of the heart and the $CO_2$ partial pressure of venous blood. With the method of the present invention, these conditions can be determined on a breath-by-breath basis. The present invention is also directed to determining changes in circulatory system conditions.

The physiological function of the heart is to circulate blood through the circulatory system to the body and lungs. For this purpose, the heart receives blood in atrial chambers during its relaxed or diastolic phase and discharges blood from its ventricle chambers during the contractile or systolic phase. The amount of blood discharged from a ventricle chamber of the heart per unit time is the cardiac output (CO). A typical cardiac output for the heart of a normal adult (at rest) is 5–6 liters per minute.

During circulation through the body, the blood is depleted of oxygen ($O_2$) and is enriched with carbon dioxide ($CO_2$) as a result of the metabolic activity of the body. A major purpose for blood circulation is to take venous blood that has been depleted in $O_2$ and enriched in $CO_2$ as a result of its passage through the tissues of the body and supply it to the lungs. In the alveoli of the lungs, $O_2$ is supplied to the blood from the breathing gases, typically air, and $CO_2$ is discharged into the breathing gases. The oxygenated arterial blood is then supplied to the body tissues. The gas exchange takes place in the capillaries of the lung because of the differences in concentration, or partial pressure, of $O_2$ and $CO_2$ in breathing gases, such as air, and in the venous blood. That is, the blood is low in $O_2$ and high in $CO_2$ whereas air is high in $O_2$ and low in $CO_2$.

To carry out the foregoing gas exchanges in the body and lungs of a subject, the heart is divided into a right side and a left side. The right side of the heart receives venous blood and pumps it to the lungs for oxygenation and $CO_2$ reduction. The left side of the heart receives the oxygenated blood from the lungs and supplies it to the arteries of the body for circulation through the tissue of the body. The cardiac output of the right and left sides of the heart is generally equal.

The regulatory mechanisms of the body respond to variations in metabolic needs of body tissue by varying the cardiac output of the heart and the amount of gas exchange occurring in the lungs to maintain a sufficient supply of oxygen to body tissue and removal of $CO_2$ from body tissue. The $CO_2$ content of the blood is an indicator of the sufficiency of gas exchange occurring in the lungs. The gas exchange occurring in the lungs depends both on the amount of blood passing through the lungs, i.e. on the cardiac output (CO), and on the amount and efficiency of gas exchange occurring in the lungs. The amount of gas exchange can be grossly altered by changing the tidal volume of the lungs, as for example, by deep breathing. However, the amount of gas exchange, and particularly the efficiency of gas exchange, also depends on the physiological condition of the lungs.

A common condition reducing the gas exchange efficiency of the lungs is the presence of shunt perfusion or blood flow in the lungs. A shunt comprises pulmonary blood flow that does not engage in gas exchange with breathing gases, due to blockage or constriction in alveolar gas passages, or for other reasons. This shunt blood flow thus bypasses normal alveoli in which gas exchange is carried out. Upon leaving the lungs, the shunt blood flow mixes with the non-shunt blood flow. The former reduces the oxygen content and increases the $CO_2$ content in the mixed arterial blood supplied to the body tissues.

It will be appreciated that only the non-shunt pulmonary blood flow through the lungs participates in the gas exchange function of the lungs and in oxygenation and $CO_2$ removal in the blood of the subject. The quantity of blood that participates in such pulmonary gas exchange in the lungs is termed functional cardiac output (FCO). For diagnostic or other purposes, it is frequently desirable or essential to know this quantity.

While shunt conditions can occur in the lungs due to blockage brought about by disease, mechanical ventilation, particularly when the respiratory muscles of a subject are relaxed as during anesthesia, can result in an increase in the pulmonary shunt. The breathing gases supplied to the lungs can be enriched with oxygen under such conditions to assist in oxygenation of the blood. However, a sufficient amount of $CO_2$ may not be removed from the blood when the pulmonary shunt is increased, giving rise to potentially adverse consequences to the subject.

The classic technique for determining the functional cardiac output of the heart is through use of the Fick equation $$FCO = \frac{VCO_2}{CvCO_2 - CcCO_2} \quad (1)$$

where,

| | |
|---|---|
| $VCO_2$ | in ml/min. is the amount of $CO_2$ released from the blood in the circulatory system of the subject, |
| $CvCO_2$ | is the mixed venous blood $CO_2$ content, for example in ml $CO_2$/ml of blood, and |
| $CcCO_2$ | is the end capillary blood $CO_2$ content, i.e. the $CO_2$ content in the blood leaving the ventilated lungs. |

The Fick equation states that, knowing the amount of $CO_2$ gas released from the blood in a unit of time (e.g. the rate of gas transfer as a volume/minute) and the concurrent gas transfer occurring per unit of blood (i.e. volume of gas/ volume of blood), the blood flow through the lungs (i.e. FCO expressed in volume/minute) can be determined.

If a portion of the pulmonary blood flow of the subject is in shunt, this will decrease the amount of $CO_2$ released from the blood and the computation of Equation (1) provides an indication of the resulting decrease in functional cardiac output. In computing functional cardiac output using the Fick equation, the quantity $VCO_2$ can be determined non-invasively by subtracting the amount of $CO_2$ of the inhaled breathing gases, for example air, from the amount of $CO_2$ of the exhaled breathing gases, taking into account changes in the amount of $CO_2$ stored in the lungs and the deadspace in the breathing organs of the subject, such as the trachea and bronchi. The amount of $CO_2$ stored in the lungs can be computed from the alveolar $CO_2$ gas concentration, as determined from an end tidal breathing gas measurement, and the end expiratory volume $V_{EE}$ of the lungs. The end capillary blood $CO_2$ content ($CcCO_2$) can be determined non-invasively, with a fair degree of accuracy, from a measurement of the concentration of $CO_2$ in the breathing gases exhaled at the end of the expiration of a tidal breathing gas volume, i.e. the end tidal (ET) $CO_2$ level. The venous blood $CO_2$ content ($CvCO_2$), is often determined invasively. An alternate non-invasive approach for the determination of the $CvCO_2$ can be seen in U.S. Pat. No. 6,042,550 and WO 01/62148. In these approaches, exhaled $CO_2$ enriched breathing gases are rebreathed by the subject in subsequent inhalations. As rebreathing of the exhaled breathings gases continues, breath-by-breath, the end tidal $CO_2$ partial pressure ($P_{ET}CO_2$) increases until the end capillary blood $CO_2$ partial pressure ($P_cCO_2$) is reached. At this point, it is postulated that the end tidal $CO_2$ partial pressure ($P_{ET}CO_2$), the alveolar $CO_2$ partial pressure ($P_ACO_2$), the end capillary blood $CO_2$ partial pressure ($P_cCO_2$), and the venous blood $CO_2$ partial pressure ($PvCO_2$) are all equal and that this partial pressure can be converted to the venous $CO_2$ content ($CvCO_2$) for use in the Fick equation.

The need for the determination of the venous blood $CO_2$ content ($CvCO_2$) is eliminated by the use of a differential form of the Fick equation which arises from the following circumstances. As a subject rebreathes exhaled breathing gases, the end tidal $CO_2$ partial pressure ($P_{ET}CO_2$) and thus the alveolar $CO_2$ partial pressure ($P_ACO_2$) and end capillary $CO_2$ content increases. This reduces the venous blood-alveolar $CO_2$ partial pressure differences and because this is the driving force for $CO_2$ elimination in the lungs, $CO_2$ elimination is also reduced. It has been shown that the ratio of the change in $CO_2$ elimination to the change in the end capillary blood $CO_2$ content is equal to the functional cardiac output. See Gedeon A., et al. Med. Biol. Eng. Comp. 18:411–418 (1980). It is set forth in equation form, as follows:

$$FCO = \frac{\Delta VCO_2}{\Delta CcCO_2}$$

which, in terms of measured quantities is expressed as $$FCO = \frac{VCO_2^N - VCO_2^R}{CcCO_2^R - CcCO_2^N} \quad (2)$$

In the differential form of the Fick equation, the superscript N indicates values obtained in "normal" breathing conditions. The superscript R indicates values obtained during a short term "reduction" in the $CO_2$ partial pressure difference between that in the alveoli and that in the blood. This results in reduced $CO_2$ transfer in the lungs.

In using the differential form of the Fick equation, a first set of values for $VCO_2$ and $CcCO_2$ are obtained, as in the manner described above, under normal breathing conditions. These are identified by the superscript N. Thereafter, the amount of $CO_2$ in the breathing gases for the subject is increased. This maybe accomplished by a partial re-breathing of exhaled breathing gases. See U.S. Pat. No. 5,836,300 and published International Patent Appln. WO 98/26710 that employ valve mechanisms for this purpose. Or, this may be accomplished by injecting $CO_2$ into the inhaled breathing gases as described in U.S. Pat. No. 4,608,995. Further possibilities for altering the alveolar $CO_2$ content include varying lung ventilation. This may be accomplished by altering the tidal volume or the respiration rate. Single breath maneuvers such as a deep breath as presented by Mitchell R R in Int J Clin Mon Comp 5:53–64 (1988), inspiratory hold as presented in WO 99/25244, or expiratory hold, may also be used for the purpose.

The $CO_2$ enrichment increases the concentration of $CO_2$ in the alveoli in the lungs and reduces the $CO_2$ partial pressure difference between that of the breathing gases in the lungs and that in the venous blood. As noted above, it is that $CO_2$ partial pressure difference that drives the $CO_2$ gas transfer from venous blood to the breathing gases in the alveoli of the lungs. The reduced $CO_2$ partial pressure difference reduces $CO_2$ gas transfer in the lung and causes an elevation of the $CO_2$ content in the blood downstream of the lung, i.e. in the arterial blood of the subject. In the time interval before the blood with elevated $CO_2$ content circulates through the body and returns to the lungs, the $CO_2$ content of venous blood ($CvCO_2$) entering the lungs can be taken to be the same for both the initial, normal breathing conditions (N) and the subsequent, reduced $CO_2$ partial pressure difference conditions labeled by the superscript R. This similitude permits the factor $CvCO_2$ to be dropped out of the Fick equation when expressed in the differential form as Equation 2 so that the cardiac output is determined by the ratio of the change in released $CO_2$ amounts ($VCO_2$) between the normal (N) and reduced (R) gas exchange conditions to the corresponding change in the end capillary blood $CO_2$ content ($CcCO_2$) in the normal and reduced (R) gas exchange conditions. The need to determine the venous blood $CO_2$ content ($CvCO_2$) from the subject is thus eliminated.

The foregoing approach is also advantageous with ventilated or anesthetized subjects since the alteration of the $CO_2$ content of the breathing gases can be effected by altering the ventilation provided to the subject. In the case of a subject anesthetized with a breathing circuit of the recirculating type, the alteration in $CO_2$ content may be carried out by bypassing the $CO_2$ absorber in the breathing circuit to increase the amount of $CO_2$ in the breathing gases that are recirculated to the subject for inspiration.

While the above described techniques avoid the need to invasively determine venous blood $CO_2$ content, other problems are created. Each time the cardiac output of the heart is measured, the $CO_2$ content of the blood is increased. This is particularly true in procedures in which the subject rebreathes only exhaled breathing gases, i.e. "total rebreathing" since there is a corresponding blockage of $CO_2$ removal or "washout" from the lungs of the subject. If the gas exchange capability of the subject's lungs is impaired, this exacerbates the problem of removing adequate amounts of $CO_2$ from the blood of the subject, particularly if the measurements are carried out frequently. A period of time is required for $CO_2$ levels in the venous and arterial blood of the subject to return to normal levels. This limits and prolongs the intervals between which functional cardiac output measurements can be taken.

Also, in cases in which a subject is being provided with a fixed volume of breathing gases, an increase in inspired $CO_2$ volume is accompanied by a decreased volume of inspired oxygen. This may produce an undesired reduction in the oxygen content in the blood or require increased oxygen concentrations in the inspired breathing gases, following a cardiac output measurement, to restore oxygen levels in the blood to desired values.

The problem of limits in rapidity with which measurement can be taken may be overcome by the technique described in published PCT application WO 00/42908. This document discloses a method for breath-by-breath determination of cardiac output and blood gas related parameters. The method is based on simultaneous measurements of oxygen and carbon dioxide quantities and the breathing gas flow. From these measurements, the instantaneous respiratory quotient (RQ) is calculated as well as the respiratory quotient integrated for a whole expiration made by the subject. The respiratory quotient (RQ) of the subject is the volume of $CO_2$ exhaled by the subject divided by the volume of $O_2$ inhaled by the subject. The expired $CO_2$ concentration at the moment the instantaneous respiratory quotient (RQ) has the value of 0.32 is then interpreted as the venous blood $CO_2$ partial pressure ($PvCO_2$). When the instantaneous respiratory quotient (RQ) equals the average respiratory quotient (RQ) for the whole expiration, the $CO_2$ concentration is identified as the arterial blood $CO_2$ partial pressure ($P_aCO_2$). The $CO_2$ partial pressures thus obtained are then converted to blood gas content. Putting these blood gas contents and the amount of $CO_2$ released from the blood ($VCO_2$) in the non-differential form of the Fick equation, Equation 1, gives the functional cardiac output.

A shortcoming of this approach is that the measurement is based on respiratory quotients (RQ) experientially obtained from a group of subjects. Also, mean respiratory quotient (RQ) characteristics are not constant and may vary depending a number of circumstances, including diet. When a subject is ventilated, further variations even beyond usual limits transiently occur for up to an hour period when ventilation to the subject is changed.

Determination of the functional cardiac output through use of the Fick equations provides significant information regarding the amount of gas exchange occurring in the lungs of the subject. In addition to this information, it is often also desired to relate lung gas exchange amounts and blood gas properties to the metabolic needs of the subject's body. If, for example, the gas exchange occurring in the lungs is insufficient as compared to the metabolic activity of the subject, $CO_2$ will accumulate in the subject's blood and the $CO_2$ content of the blood will rise. Clinicians may therefore wish to look at the levels of $CO_2$ and other gases in the blood of a subject. Thus, while the differential form of the Fick equation is designed to eliminate the need to measure $CO_2$ levels in venous blood when determining functional cardiac output, there may still exist a need for this information for other medical purposes.

Historically, $CO_2$ levels in venous blood have been obtained by invasively removing a blood sample from the subject and using a blood gas analyzer to analyze the gaseous properties of the blood sample. A blood gas analyzer typically expresses these properties as the partial pressures of the various gases in the blood. The use of partial pressures is based on Dalton's law which states that in a mixture of gases, such as $O_2$, $N_2$, $CO_{02}$, etc., in a container or in a medium, such as blood, the pressure exerted by each gas, i.e. its partial pressure, is the same as that which the gas would exert if it alone occupied the container or medium. This allows the partial pressure of a gas to serve as an expression of gas quantity. Physicians, and other clinicians, have become accustomed to seeing and working with blood gas properties expressed as partial pressures rather than as gas content expressed volumetrically or otherwise. Thus, while determination of functional cardiac output requires blood gas content, in many other instances it is desired to express blood gas properties as partial pressures. That is, an arterial $CO_2$ blood quantity could be expressed as a partial pressure, for example, $PaCO_2$, rather than as a content, $CaCO_2$, or a venous property could be expressed as a partial pressure as, $PvCO_2$, rather than as a content, $CvCO_2$.

However, in relating blood $CO_2$ contents and blood $CO_2$ partial pressures, there is often a failure to recognize that the levels of different gases in the blood are interrelated. Thus, the higher the $O_2$ level in the blood, the lower the capacity of the blood to transport $CO_2$. Stated in a different way, if the amount of $CO_2$ in the blood is to remain constant as the $O_2$ content of the blood changes, for example, increases, the $CO_2$ partial pressure must also change, i.e. also increase. This phenomenon is known as the Halldane effect and failure to take this effect into account will affect the accuracy by which, for example, the $CO_2$ partial pressure of venous blood ($PvCO_2$) can be determined from $CO_2$ blood content measurements obtained from the subject.

A common shortcoming of discrete measurements of circulatory system conditions of the above type is the ignorance of a value, such as functional cardiac output, between the measurements. Cardiac output or functional cardiac output remain unchanged as long as both the $CO_2$ elimination and the venous to arterial (or end-capillary) $CO_2$ content difference remain unchanged. The $CO_2$ elimination and the end-tidal $CO_2$ fraction from which the $CcCO_2$ can be determined can be measured on breath-by-breath basis, but the changes in $CvCO_2$ for use in Fick Equation 1 remain undetected.

An approach to dealing with this shortcoming is noted in U.S. Pat. No. 6,238,351, which discloses a method to compensate the venous to arterial $CO_2$ content difference for changes that can be detected. These changes include changes in ventilation, $CO_2$ elimination, end-tidal $CO_2$, and time. However, a problem with such a method is to determine the degree of compensation needed when a change is detected in one or more of the detected parameters.

BRIEF SUMMARY OF THE INVENTION

An object of the present invention is to provide an improved method for non-invasively determining the functional cardiac output of a subject. A more particular object of the present invention is to provide a method for non-invasively determining functional cardiac output on a breath-by-breath basis so that such information is available to a clinician on a real time basis.

A further object of the present invention is to provide a method for simply and accurately determining $CO_2$ characteristics of the blood, such as the $CO_2$ partial pressure of venous blood ($PvCO_2$). Further, with the method of the present invention, characteristics, such as $PvCO_2$, can be determined on a breath-by-breath, real time, basis.

Another object of the present invention is to provide a method that can make such determinations in a manner that avoids the undue build up of $CO_2$ in the blood of the subject that has heretofore hindered such measurements.

Yet another object of the present invention is to provide a method to assess the validity of a circulatory system condition value, such as cardiac output, functional cardiac output, or $CO_2$ partial pressure of venous blood ($PvCO_2$) after a discrete measurement of same has been made and to detect changes in such a value with time.

Briefly, in accordance with one aspect of the improved method of the present invention, the amount $CO_2$ in the breathing gases exhaled by the subject and the end tidal (ET)

$CO_2$ concentration of the exhaled breathing gases are measured. This is typically done for normal breathing by the subject and the measurements are labeled with an (N) for "normal." The normal breathing by the subject establishes a concentration of $CO_2$ in the lungs of the subject. Using the amount of $CO_2$ in the exhaled breathing gases, at least one value of the amount of $CO_2$ released from the circulatory system of the subject ($VCO_2^N$) is determined. Using the end tidal (ET) $CO_2$ concentration of the breathing gases exhaled by the subject at least one value of the end capillary blood $CO_2$ content of the subject ($CcCO_2^N$) or a quantity indicative of same is also determined.

The concentration of $CO_2$ in the lungs of the subject is then changed or altered. This may be accomplished by increasing the $CO_2$ content of the breathing gases inhaled by the subject. This increases the $CO_2$ concentration in the lungs of the subject, reducing $CO_2$ gas exchange in the lungs of the subject. The amount of $CO_2$ and the end tidal (ET) $CO_2$ concentration of the breathing gases exhaled by the subject is measured for at least one breath of the subject under these conditions and the measurements labeled with an (R) for "reduced" gas exchange. From these measurements, a value for the amount of $CO_2$ released from the circulatory system of the subject ($VCO_2^R$), and a value for the end capillary blood $CO_2$ content ($CcCO_2^R$) of the subject or quantity indicative of same are obtained in the same manner as the N values. The R values are determined from gas measurements from a time period less than that required for blood leaving the lungs of the subject to pass through the circulatory system of the subject and return to the lungs.

A regression analysis is then performed using the obtained $VCO_2^N$, $VO_2^R$ and $CcCO_2^N$, $CcCO_2^R$ values for normal and reduced gas exchange breathing to establish a regression line. The slope of the regression line represents the functional cardiac output (FCO) of the subject, as determined by a differential form of the Fick equation.

Further in accordance with the present invention, the regression line is extrapolated to obtain a value for the end capillary blood $CO_2$ content ($CcCO_2$), or quantity indicative of same, when the amount of $CO_2$ released from the circulatory system of the subject ($VCO_2$) is zero. Under conditions in which no $CO_2$ is released from the circulatory system of the subject, the $CO_2$ content of venous blood will be the same as that of the end capillary blood ($CcCO_2$), so that the former quantity ($CvCO_2$) now becomes known from the latter quantity. The venous blood $CO_2$ content ($CvCO_2$) thus determined can be inserted in the Fick Equation 1, along with the $VCO_2$ values and $CcCO_2$ values measured from the subject's subsequent normal breathing to compute the functional cardiac output of the subject.

Due to the $CO_2$ buffering action of the subject's body, the $CO_2$ content of venous blood remains relatively constant or changes only slowly with time. This allows the value for the $CO_2$ content of venous blood ($CvCO_2$) determined in the above manner to be used to ascertain the functional cardiac output of the subject for subsequent breaths of the subject on a breath-by-breath basis by solving the Fick Equation 1 using newly obtained values for $VCO_2$ and $CcCO_2$ measured in the subsequent breaths.

The accuracy by which these subsequent determinations can be made can be improved by adjusting or calibrating the $CvCO_2$ value based on values for $CcCO_2$ obtained from measurements taken in subsequent breaths. To this end, a relationship is established between the value for $CvCO_2$ determined in the above manner and the value for $CvCO_2^N$ used in the linear regression and extrapolation that establishes that $CvCO_2$ value. The relationship established may be a ratio or a difference. The relationship is then applied to values of $CcCO_2$ obtained from subsequent breaths to correspondingly alter the $CvCO_2$ value. The new, altered, value for $CvCO_2$ is then used in the Fick Equation 1, along with $VCO_2^N$ and $CcCO_2^N$ values obtained from the subsequent breaths to determine functional cardiac output with improved accuracy.

The invention has been described, above, in an embodiment in which the alteration in lung $CO_2$ concentration needed to establish the data points used in the regression analysis has been obtained by changing the concentration from a lower concentration to a higher concentration. That is, the lung $CO_2$ concentration existing in normal (N) breathing is increased by the reduced (R) lung gas exchange conditions. However, it is also possible to practice the method of the present invention in a manner in which the lung $CO_2$ concentration is changed from a higher concentration to a lower concentration in order to establish the regression data points. For example, a subject with diseased lungs and breathing with a mechanical ventilator may often breath with reduced tidal air flows to reduce trauma to the lungs or thoracic cavity from movement of the lungs. This results in elevated lung $CO_2$ concentrations and reduced $CO_2$ gas exchange. Values for $VCO_2$ and $CcCO_2$ are obtained under these conditions. Thereafter, the ventilation of the subject's lungs is temporarily increased. This will lower the lung $CO_2$ concentration and increase $CO_2$ gas exchange. Values for $VCO_2$ and $CcCO_2$ are again obtained for use in the regression analysis.

Thus, the two sets of values used in the regression analysis can be obtained by either altering the lung $CO_2$ concentration from a lower value to a higher value or from a higher value to a lower value.

The method of the present invention has been described above using the end capillary blood content ($CcCO_2$) for exemplary purposes. However, since end tidal $CO_2$ concentration, the end capillary blood $CO_2$ content ($CcCO_2$), and the end capillary blood $CO_2$ partial pressure all bear a fixed relationship to each other, appropriate values for any of these quantities can be used in the denominator of the Fick Equation 1, with appropriate coefficients, to solve the equation.

To determine the $CO_2$ partial pressure of venous blood ($PvCO_2$), the venous blood $CO_2$ content ($CvCO_2$), determined as described above, is altered in accordance with the amount of oxygen in the venous blood, to correctly indicate the $CO_2$ partial pressure of the venous blood. By using a $CvCO_2$ value which is adjusted or calibrated in accordance with subsequent $CcCO_2$ values, an accurate indication of the venous blood $CO_2$ content ($PvCO_2$) of the subject can be provided on a breath-by-breath basis.

In accordance with another aspect of the present invention, an improved method and apparatus are provided to determine changes in the condition of the circulatory system of a subject, as determined by the foregoing, or other, techniques. This aspect of the present invention employs variables capable of indicating the circulatory system condition of the subject. Quantities, such as the amount $CO_2$ in the breathing gases exhaled by the subject and/or the end tidal (ET) $CO_2$ concentration of the exhaled breathing gases, may be used for this purpose and may be the values obtained for normal (N) breathing by the subject. Values for other available indicator variables, such as heart rate, may also be used.

Simultaneously with, or following, the obtaining initial values for the indicator variables, a discrete measurement of the circulatory system condition of the subject, such as cardiac output (CO) or functional cardiac output (FCO) is performed. As noted above, this may be done non-invasively by altering the alveolar $CO_2$ level and thereby the $CO_2$ elimination from blood to alveoli, i.e. from the (N) condition to the (R) condition. This disturbance can be done by increasing inspiratory $CO_2$ concentration by rebreathing expired gas or adding $CO_2$ to the inspired gas or by altering ventilation, or by single breath maneuvers like a deep breath or breath hold. The measurement can also be carried out invasively, as for example, using a blood dilution technique such as thermodilution to measure cardiac output (CO).

After the initial indicator variable value or values have been obtained and the discrete measurement has been performed, corresponding indicator variable values are obtained for subsequent breaths and/or heart beats of the subject. These subsequently measured indicator variable values are then compared with the initially obtained values to determine whether a change has occurred. If a change is detected, a desired action may be initiated. Such action may include an automatic re-measurement of the measured circulatory system condition. Or, an indication of the change and/or the direction of the change in the measured quantity or an alert of the invalidity of the previously measured circulatory system condition may be provided to a clinician attending the subject.

Various other features, objects, and advantages of the invention will be made apparent from the following detailed description and the drawings.

BRIEF DESCRIPTION OF THE SEVERAL VIEWS OF THE DRAWING

In the drawing:

FIGS. 5 and 5A is a flow chart showing a method of the present invention.

DETAILED DESCRIPTION OF THE INVENTION

The basic principles on which the method of the present invention is based are as follows. For one or more normal (N) breaths of the subject, values are obtained for the amount of $CO_2$ released from the blood ($VCO_2^N$) and for a quantity indicative of the end capillary blood $CO_2$ content, for example $CcCO_2^N$. One or more values for the same quantities are obtained under conditions of reduced (R) gas exchange in the lungs of the subject, to comprise $VCO_2^R$ and $CcCO_2^R$ values. The $CO_2$ content of the inhaled breathing gases may be increased to obtain the latter values and thereafter reduced to that for normal breathing.

Figure 1:
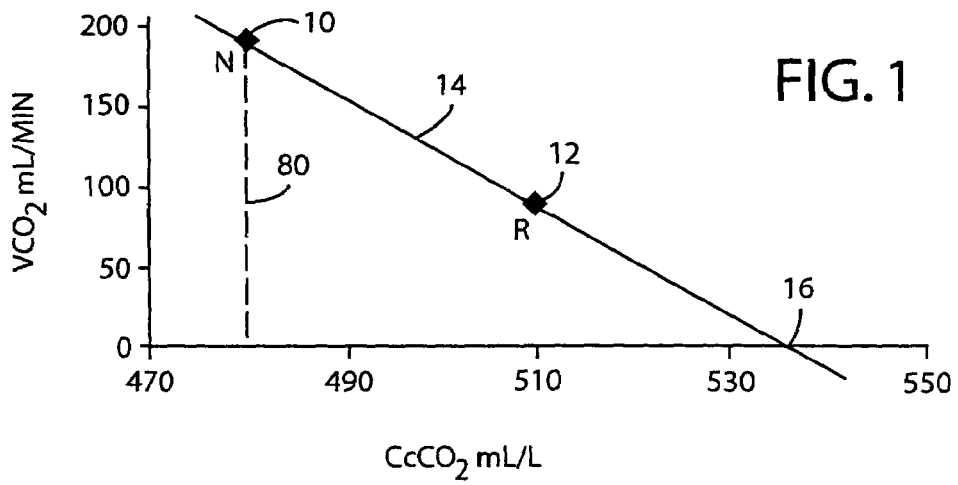
FIG. 1 is a graph showing data obtained from the breathing gases of a subject under normal breathing conditions and under conditions of reduced gas exchange in the lungs of the subject.

The normal (N) breathing values (N) and reduced (R) gas transfer values (R) are used as data points for a regression analysis, such as a linear regression analysis. Graphically, the data points may be plotted on a graph in which the end capillary $CO_2$ blood quantity values, such as $CcCO_2$, are scaled along the abscissa and values for the released amount of $CO_2$ ($VCO_2$) are scaled along the ordinate. Such a graph is shown in FIG. 1. For simplicity only, a single set of N and R data points are shown in FIG. 1 as points 10 and 12, respectively. The regression analysis produces a straight line 14 providing the best fit for the data points. In the simplified example shown in FIG. 1, this is a straight line intersecting the two data points. The downward slope of line 14 makes it clear that the greater the amount of $CO_2$ that is released in the exhalations of the subject, the less will be the end capillary blood $CO_2$ content of the subject.

It will also be appreciated that the slope of line 14 represents the functional cardiac output of the subject as expressed in the differential form of the Fick equation, Equation 2. That is, the difference between the amount of $CO_2$ ($VCO_2$) released under normal (N) conditions and that released under reduced (R) gas transfer conditions shown along the ordinate of FIG. 1 represents the numerator of Equation 2. The corresponding situation exists with respect to the difference in end capillary blood $CO_2$ content ($CcCO_2$) shown on the abscissa of FIG. 2 and forming the denominator of Equation 2. When Equation 2 is presented graphically in the manner shown in FIG. 1, the functional cardiac output thus determined will have a negative sign due to the transposition of the quantities forming the denominator of the equation.

In the method of the present invention, regression line 14 is extended or extrapolated to cross the abscissa of FIG. 1 along which the $CcCO_2$ values are graphed. This point is shown as point 16 in FIG. 1. Point 16 on the abscissa of the graph of FIG. 1, represents a state in which the amount of $CO_2$ released from the lungs ($VCO_2$) is zero and provides an indication of the end capillary blood $CO_2$ content ($CcCO_2$) under such conditions. In the example shown in FIG. 1, this end capillary blood content ($CcCO_2$) is approximately 536 ml per liter of blood.

Under conditions in which no $CO_2$ is released from the blood of the subject to the alveolar breathing gases, the end capillary blood $CO_2$ content ($CcCO_2$) will equal the venous blood $CO_2$ content ($CvCO_2$). Knowing the venous blood $CO_2$ content ($CvCO_2$) enables the functional cardiac output (FCO) of the subject to be determined from Fick Equation 1 using this $CvCO_2$ value and $VCO_2$ and $CcCO_2$ values determined from the breathing of the subject.

Thus, by using the method of the present invention, the functional cardiac output can be determined by Fick Equation 1 without requiring the total rebreathing of exhaled breathing gas, as proposed in the '550 patent to obtain a value for $CvCO_2$. Total rebreathing results in the elevated $CO_2$ blood levels that may be harmful to the patient and must be lowered before the functional cardiac output can again be determined. Since a number of breaths are required to restore $CO_2$ content to normal levels, this limits the measurement interval and prolongs the interval between FCO measurements. It also avoids the problem that the oxygen content of the re-breathed gases may be reduced in order to maintain constant breathing gas volumes. This may reduce oxygen levels in the blood of the subject and may require increased oxygen concentration in the inspired breathing gases immediately following a cardiac output measurement to restore oxygen levels in the blood to desired levels. With the method of the present invention, the elevation in breathing gas and blood $CO_2$ levels need be no greater than that required to provide R values that enable the regression analysis to be accurately carried out.

Figure 2:
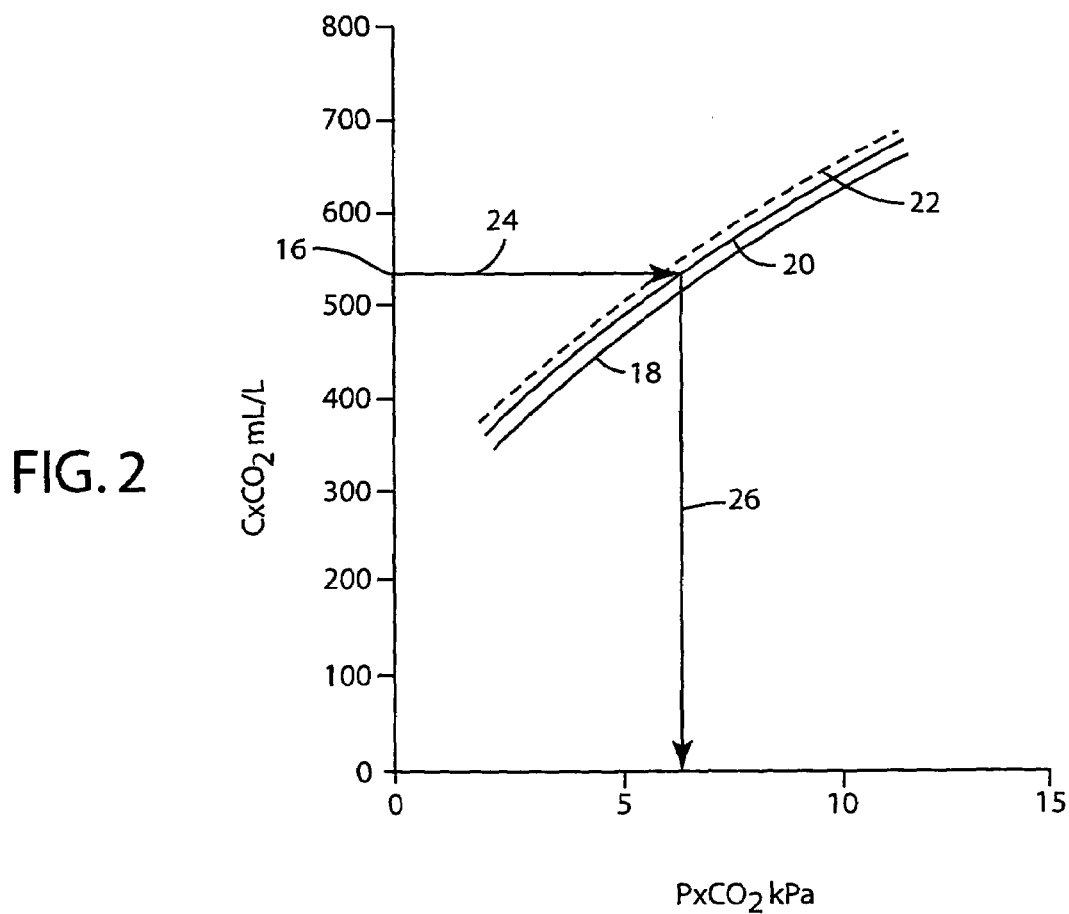
FIG. 2 is a graph showing the relationship between the $CO_2$ content of blood and the $CO_2$ partial pressure of blood.

Also, by knowing the venous blood $CO_2$ content ($CvCO_2$) it is possible to determine the venous blood $CO_2$ partial pressure ($PvCO_2$). This is done with the aid of the relationships set out in graphic form in FIG. 2. FIG. 2 presents blood $CO_2$ partial pressures on the abscissa as a function of blood $CO_2$ content on the ordinate. The quantities are labeled $P_X$ and $C_X$ to indicate that the curves in the graph can be used for both arterial as well as venous blood. Use of the present invention to analyze the gas properties of venous blood is particularly advantageous in view of the difficulties heretofore encountered in obtaining these properties and is thus described below for exemplary purposes.

Blood $CO_2$ content is affected by the $O_2$ content of the blood, a circumstance described as the Halldane effect. Thus, the higher the $O_2$ level in the blood, the lower the capacity of the blood to transport $CO_2$. Stated in a different way, if the amount of $CO_2$ in the blood is to remain constant as the $O_2$ content of the blood changes, for example, increases, the $CO_2$ partial pressure must also change, i.e. also increase. If the $CO_2$ partial pressure for venous blood is to be accurately determined, the foregoing circumstance prevents simple substitution of $CvCO_2$ for $PvCO_2$ due to the errors introduced by the Halldane effect.

The steps of the present invention shown in FIG. 2 enable the $CO_2$ partial pressure of the blood to be accurately established from the $CO_2$ content of the blood. In the graph of FIG. 2, the blood $CO_2$ content, such as $CcCO_2$, is shown on the ordinate. This is the same quantity that is scaled on the abscissa of the graph of FIG. 1. The abscissa of the graph of FIG. 2 is scaled in blood $CO_2$ partial pressure. The lines 18, 20, 22 in the graph of FIG. 2 relate blood $CO_2$ content to blood $CO_2$ partial pressure for various oxygenation conditions in the blood. It is convenient to express blood oxygenation as oxygen saturation of the hemoglobin (Hb) in the blood ($SO_2$). Hemoglobin is found in the red corpuscles of the blood and serves to carry oxygen from the lungs to the body tissues. The lines 18, 20, and 22 can be established using known medical data relating blood $CO_2$ content to blood $CO_2$ partial pressures for various oxygen levels in the blood. See, for example, *Respiratory Physiology*, by J. F. Nunn, published 1993 by Butterworths. Or the relationships expressed by lines 18, 20, and 22 may be determined experimentally from blood samples. Line 18 shows the $CxCO_2$—$PxCO_2$ relationship when arterial blood has 100% hemoglobin oxygen concentration ($SO_2$). Line 20 is used to establish the relationship between blood $CO_2$ content ($CxCO_2$) and blood $CO_2$ partial pressure ($PxCO_2$) when the blood is at 65% oxygen saturation and line 22 is used when the blood is at 30% oxygen saturation. It will be appreciated that lines can be established for all desired oxygenation conditions of the blood.

In FIG. 2, point 16 shown on the abscissa of FIG. 1 has been transposed to the ordinate of FIG. 2 and again shown as point 16. The graph of FIG. 2 thus becomes one relating the venous blood $CO_2$ content ($CvCO_2$) (and end capillary blood $CO_2$ content ($CcCO_2$)) at zero $CO_2$ release ($VCO_2$) to the $CO_2$ partial pressure of venous blood ($PvCO_2$). The intersection of a horizontal line 24 drawn from point 16 in FIG. 2 to the appropriate curve in the graph of FIG. 2 and dropped to the abscissa by vertical line 26 will provide the $CO_2$ partial pressure in venous blood ($PvCO_2$) for the blood oxygen condition represented by the curve. For example, when it is known that venous blood is at 65% hemoglobin oxygen saturation, the intersection of line 24 and curve 20 extended via line 26 to the abscissa of FIG. 2 will indicate the $CO_2$ partial pressure ($PvCO_2$) of the subject's blood to be about 6 kPa.

The principles of the method of the present invention illustrate how the $CO_2$ content of venous blood ($CvCO_2$) can be determined from the end capillary blood $CO_2$ content ($CcCO_2$) at zero release of $CO_2$ from the blood of the subject, i.e. $VCO_2$ equals zero. It will be appreciated that if it is desired to determine the end tidal $CO_2$ concentration ($F_{ET}CO_2$) under zero $CO_2$ release conditions, the same principles as described above can be used simply by scaling the abscissa of FIG. 1 in end tidal $CO_2$ concentration and plotting N and R data using $VCO_2$ and $F_{ET}CO_2$ values. Further, since the $CO_2$ partial pressure of end capillary blood bears a known relation to the end tidal $CO_2$ concentration, the $CO_2$ partial pressure of end capillary blood ($PcCO_2$) at zero release of $CO_2$ from the blood of the subject can also be determined by applying the known relationship.

These other quantities, indicative of the end capillary blood $CO_2$ content, can also be used to determine the functional cardiac output of the subject using an equation of the Fick Equation 1 type in a manner analogous to that described above and applying appropriate coefficients to the end tidal $CO_2$ or end capillary blood $CO_2$ partial pressure values inserted in the equation.

Figure 3:
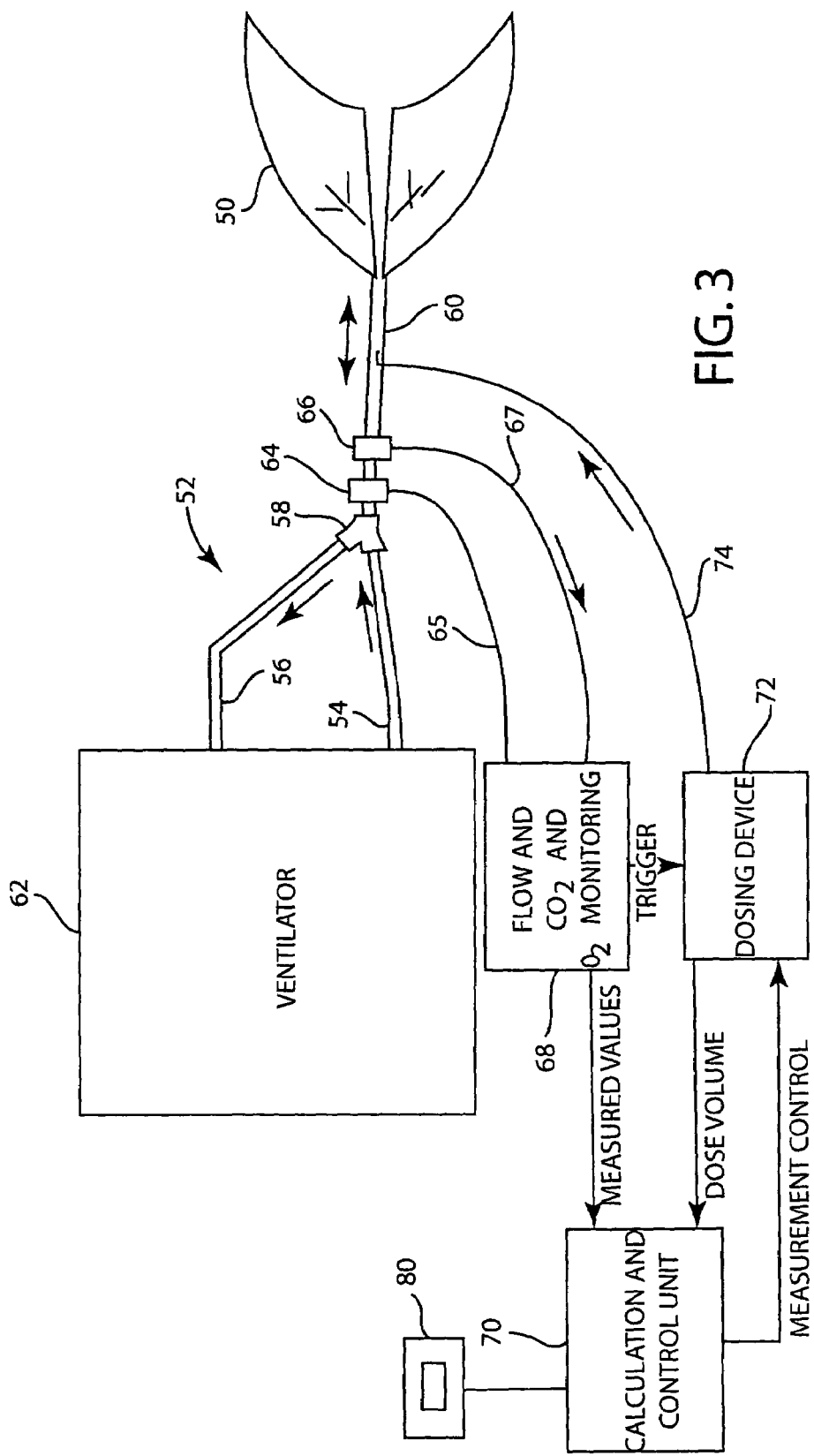
FIG. 3 is a schematic diagram of apparatus suitable for practicing the method of the present invention.

FIG. 3 shows apparatus suitable for carrying out the method of the present invention using mechanical ventilating equipment. The breathing organs of the subject, including lungs 50 are supplied with breathing gases through breathing circuit 52 of conventional construction. Breathing circuit includes inspiration limb 54 that supplies breathing gases to the subject and expiration limb 56 that receives exhaled breathing gases from the subject. Inspiration limb 54 and expiration limb 56 are connected to two arms of Y-connector 58. A third arm of Y-connector 58 is connected to patient limb 60. Patient limb 60 supplies and receives breathing gases to/from the subject through an endotracheal tube, face mask, or other appliance (not shown).

The other ends of inspiration limb 54 and expiration limb 56 are connected to ventilator 62. Ventilator 62 provides breathing gases in inspiration limb 54 and receives breathing gases from expiration limb 56.

In the usual manner of a breathing circuit, patient limb 60 contains various breathing gas sensing and other apparatus. Patient limb 60 may contain flow sensor 64 for measuring breathing gas flows to and from the subject. A flow measuring apparatus suitable for use in breathing circuit 52 is shown in U.S. Pat. No. 5,088,332 to Instrumentarium Corp. of Helsinki, Finland. A hot wire anemometer may also be used for this purpose.

Patient limb 60 also contains quantitative gas sensing apparatus 66 for measuring the composition of the breathing gases to/from the patient. Such gas sensing apparatus includes a $CO_2$ sensor for measuring the amount of $CO_2$ in the breathing gases and end tidal $CO_2$ concentrations. The $CO_2$ sensor typically comprises apparatus using infrared radiation. Such equipment may comprise a gas monitoring module M-GAS made and sold by Datex-Ohmeda Division of Instrumentarium Corp. of Helsinki, Finland.

The output of sensors 64 and 66 are provided in sampling lines 65 and 67 to signal processing unit 68 in which integration of flow rates to obtain volumes, filtering, or other signal processing is carried out to produce values for the sensed quantities. Signal processing unit 68 is connected to calculation and control unit 70. The necessary integration, filtering, etc. of the signals from sensors 64 and 66 may be carried out in the calculation and control unit 70. Signal processing unit 68 may also include means for determining when inhalation by the subject commences. The flow sensor 64 or a pressure sensor may be used for this purpose to sense the incipient flow of breathing gas toward the patient or pressure change that characterizes the initiation of inhalation.

FIG. 3 shows apparatus in which the increased lung $CO_2$ concentrations in breathing gases are obtained by injecting $CO_2$ into the inhaled breathing gases. To this end, dosing apparatus 72 is connected to $CO_2$ supply line 74 to inject $CO_2$ into the breathing gases inhaled by the subject. Dosing device 72 is connected to a supply of $CO_2$ (not shown). $CO_2$ supply line 74 terminates in the flow path for the subject's breathing gases, downstream of sensors 64 and 66, as shown in FIG. 3. Dosing apparatus 72 may comprise apparatus of the type shown in U.S. Pat. Nos. 5,918,596 and 6,131,572 owned by the Instrumentarium Corp. of Helsinki, Finland that enable the delivered amount of $CO_2$ to be accurately determined. Dosing apparatus 72 is connected to calculation and control unit 70 and the amount of $CO_2$ injected is determined by calculation and control unit 70. Dosing device 72 may provide dosing volume feedback data to calculation and control unit 70 for use in controlling the operation of dosing apparatus 72. Signal processing unit 68 provides a trigger signal to dosing apparatus 72 for initiating the administration of $CO_2$ during inhalation by the subject. Typically, this would be at the onset of the inspiration of breathing gases into the lungs of the subject. Or, a signal from ventilator 62 may be provided to dosing apparatus 72 for this purpose.

Calculation and control unit 70 contains a microprocessor or other suitable element for carrying out the technique of the invention described in connection with FIGS. 1 and 2.

Sensors 64 and 66 and signal processing unit 70 measure gas flows, expired $CO_2$ concentrations, and end tidal $CO_2$ gas concentrations. Measured expired $CO_2$ concentrations and gas flows can be used to determine the amount of $CO_2$ ($VCO_2$) released from the blood. The end tidal $CO_2$ concentration is used to determine quantities indicative of the $CO_2$ content of the blood, such as $CcCO_2$, as described above.

The method for carrying out the method of the present invention is as follows. The method is described as in an instance using air as the breathing gases. Respiration may be either spontaneous on the part of the subject or assisted by the ventilation apparatus shown in FIG. 3.

The subject breathes, or is ventilated, with breathing gases such as air. The normal (N) breathing action of the subject is allowed to stabilize. This may, for example, require a minimum of five breaths or a half a minute to a minute of time. The amount of $CO_2$ released from the blood in the lungs of the subject and the $CO_2$ concentration in the breathing gases are then measured, for at least one breath, or preferably for each of a plurality of breaths, of the subject. Typically, the $CO_2$ concentration is measured as the end tidal $CO_2$ concentration ($P_{ET}CO_2^N$). One or more values of $VCO_2$ (N) are determined. In this exemplary description, the quantity used to describe the end capillary blood $CO_2$ condition is the $CO_2$ content ($CcCO_2$). The measured end tidal $CO_2$ concentrations are thus used to determine $CcCO_2$ and one or more $CcCO_2$ N values are obtained from the end tidal $CO_2$ levels for the breaths.

Thereafter, the $CO_2$ content of the breathing gases inhaled by the subject is increased to increase the $CO_2$ concentration in the lungs of the subject and to reduce $CO_2$ gas transfer. Using the apparatus shown in FIG. 3, this may be accomplished by administering a bolus of $CO_2$ into the inhaled breathing gases each time the subject breathes. Or, the subject may engage in re-breathing of breathing gases previously exhaled by the subject.

The end tidal $CO_2$ levels are examined as the subject breaths under these conditions. When the end tidal $CO_2$ levels no longer change, this indicates that the alveolar $CO_2$ concentration in the lungs is constant which means that $CO_2$ storage in the lungs has been accommodated. The measurement of the amount of gas released from the lungs of the subject and $CO_2$ concentrations of the breathing gases, i.e. end tidal $CO_2$ concentration, is then commenced. After measurements are taken, the enrichment of $CO_2$ in the inhaled breathing gases may thereafter be terminated and $CO_2$ concentrations in the lungs allowed to return to normal levels.

The exact amount and duration of the $CO_2$ enrichment will depend on numerous physical and physiological factors of the patient and on the data needed to accurately determine functional cardiac output. For injected $CO_2$ the amount is typically 5 ml to 30 ml per breath occurring over several breaths, for example, those taken in 20 seconds to one minute in time. For a typical adult, $CO_2$ would be injected in about 6 or 7 breaths.

The amount of $CO_2$ provided in the boluses is governed by somewhat conflicting considerations. The larger the boluses, the larger will be the alveolar $CO_2$ concentration in the lungs and the end capillary blood $CO_2$ content ($CcCO_2$). This will place the R data point 12 closer to the intersection of line 14 with the abscissa of FIG. 1 at point 16 and improve the accuracy by which $CvCO_2$ can be determined. On the other hand, the more $CO_2$ that is delivered, the less $CO_2$ gas exchange occurs in the lungs of the subject resulting in higher $CO_2$ blood levels that require a longer time to return to normal levels. The amount of $CO_2$ delivered to the subject represents an optimum combination of these factors and need be no greater than that required to achieve the desired results.

The amount of $CO_2$ released from the blood of the subject ($VCO_2^R$) is determined by subtracting the amount of $CO_2$ in the enriched, inhaled breathing gases from the $CO_2$ amount measured in the exhaled breathing gases. The measured end tidal $CO_2$ levels are used to determine the end capillary blood $CO_2$ content $CcCO_2^R$. These determinations are carried out from measurements obtained within the circulation period of the blood in the body of the subject following the administration of the boluses. This is a period of approximately 30 seconds to one minute. In this period, the venous blood $CO_2$ content ($CvCO_2$) remains constant since it has not yet returned to the lungs to undergo gas exchange.

If desired, an administration of increased $CO_2$ in the inhaled breathing gases to the subject can be repeated after an appropriate interval during which $CO_2$ levels in the blood return to normal.

A regression analysis, such as a linear regression analysis, is then performed using the normal (N) values obtained from the initial breaths of the patient and the reduced (R) gas transfer values obtained following the increase in the $CO_2$ content of the inhaled breathing gases. It will be appreciated that the data used to perform the regression analysis can include many normal (N) values obtained from the plurality of normal breaths taken by the patient. There will be a smaller number of R values since usually only one R value is obtained each time the $CO_2$ content of the inhaled breathing gas is increased.

As noted above, the slope of line 14 produced by the regression analysis is the negate of the functional cardiac output (FCO) of the patient.

The intersection of line 14 with the abscissa of FIG. 1 is then determined to provide an end capillary blood ($CcCO_2$) value for condition of zero $CO_2$ release ($VCO_2$) from the blood and the corresponding venous blood $CO_2$ content ($CvCO_2$).

The venous $CO_2$ content ($CvCO_2$) determined, as described above, is then used for further determination of the functional cardiac output by using the non-differential form of the Fick equation, Equation 1, above. To this end, the quantity $CvCO_2$ is inserted in Fick Equation 1. Measured $CO_2$ release ($VCO_2$) values and end capillary blood $CO_2$ ($CcCO_2$) values taken from subsequent breaths and representing normal (N) values of these quantities are also inserted in Fick Equation 1 to compute of the functional cardiac output from these subsequent breaths.

The solution result of the Fick Equation 1 will remain accurate for as long as the determined value of $CvCO_2$ remains accurate. Since the body of the subject buffers changes in $CO_2$ in the body, this allows $CvCO_2$ to remain relatively constant for a useful period of time.

The accuracy of the value for venous blood $CO_2$ content ($CvCO_2$) used in solving Fick Equation 1 along with data from subsequent breaths of the subject, can be improved by adjusting or calibrating the value in the manner described below. These techniques are based on establishing a relationship between the value of venous blood $CO_2$ content ($CvCO_2$), determined as described above, and the normal (N) breathing end capillary $CO_2$ content ($CcCO_2^N$) used in that determination. This relationship is then used to adjust or calibrate the venous blood $CO_2$ content ($CvCO_2$) when new end capillary blood $CO_2$ content ($CcCO_2$) values are obtained from subsequent breaths of the subject.

For example, it will be seen from an inspection of FIG. 1 that a venous blood $CO_2$ content ($CvCO_2$) value of approximately 536 ml/l (the intersection 16 of line 14 with the abscissa of FIG. 1) is obtained when the normal (N) value for the end capillary blood $CO_2$ content ($CcCO_2$) is approximately 480 ml/l. This quantity is obtained by determining the X axis coordinate for normal N point 10 as shown by dotted line 80 in FIG. 1. Placing $CvCO_2$ in a numerator and $CcCO_2^N$ in a denominator provides a ratio between the two values, which in this example has a numerical value 1.13.

In the computation of functional cardiac output using Fick Equation 1, newly determined $CcCO_2^N$ values obtained from subsequent normal (N) breaths of the subject are multiplied by the quantity 1.13 to obtain new $CvCO_2$ values to be used in Fick Equation 1, thereby improving the accuracy with which functional cardiac output is determined.

Another technique that may be used in accurately solving Fick Equation 1 is as follows. Using the $CvCO_2$ value obtained in the manner described above, and illustrated in FIG. 1, and the corresponding X axis coordinate value for $CcCO_2^N$, the difference between these values along the X axis is determined. In the numerical example shown in FIG. 1, the value for $CvCO_2$ is 536 ml/l and for $CcCO_2^N$ is 480 ml/l. The difference is 56 ml/l. Thereafter, this amount is applied to $CcCO_2^N$ values obtained in subsequent normal (N) breaths from the subject, i.e. the difference amount, such as 56, is added to the $CcCO_2^N$ values obtained from the subsequent breaths of the subject to obtain the new $CvCO_2$ values which are used in the solution of Fick Equation 1.

The calibration techniques described above enables the $CvCO_2$ value to follow the $CcCO_2^N$ quantities obtained by measurements taken in the subsequent breaths of the patient. This improves the accuracy by which the functional cardiac output (FCO) of the subject can be determined.

To determine functional cardiac output on a breath-by-breath basis, the $VCO_2$ and $CcCO_2$ data obtained for each normal (N) breath of the subject is entered in Fick Equation (1), along with the $CvCO_2$ value determined in one of the various ways described above. The computation of functional cardiac output is then carried out using the data for that breath. The use of subsequently obtained normal (N) breathing end capillary blood $CO_2$ content ($CcCO_2^N$) to calibrate or adjust the venous blood $CO_2$ ($CvCO_2$) value used in Fick Equation 1 allows the functional cardiac (FCO) to be determined on a real time basis over an extended period of time. And, as noted above, this is accomplished without the undue increase the $CO_2$ content of the subject's blood that has occurred in the past.

If significant changes occur in the breathing conditions for the subject, for example, a change in the settings of ventilator 62, or in patient metabolism, or in disease status, the original steps of the method must again be carried out to obtain a new value for the venous blood $CO_2$ content ($CvCO_2$) to be used in the computation of functional cardiac output.

Figure 4:
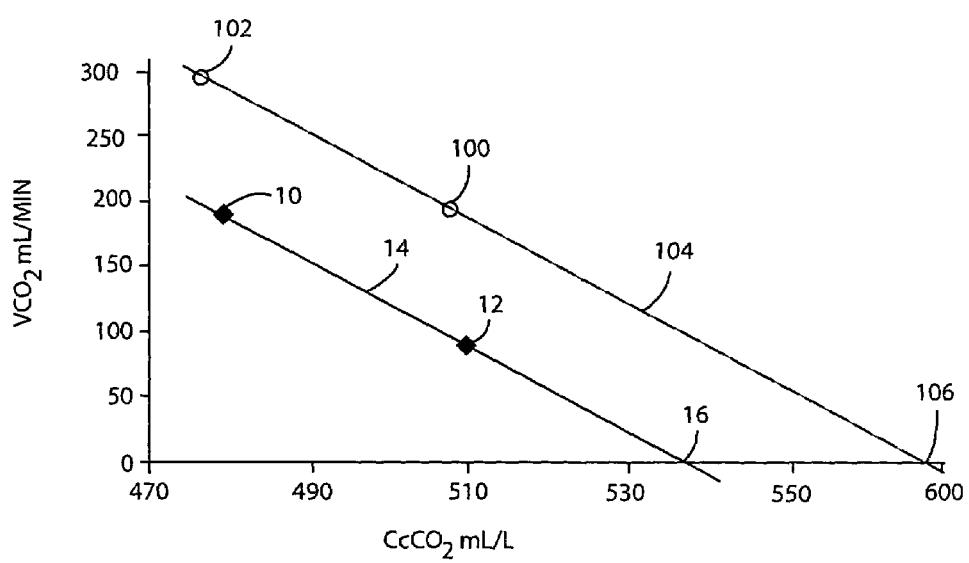
FIG. 4 is a graph incorporating FIG. 1 and showing data obtained in a modification of the method of the present invention.

In the method described above, the alteration in the $CO_2$ concentration in the lungs necessary to obtain the regression analysis data points has been obtained by increasing the $CO_2$ lung concentration as a result of the subject breathing $CO_2$ enriched breathing gases. However, since what is needed in the method of the present invention is two different lung $CO_2$ concentrations to obtain the two data points, it is equally possible to practice the invention in a manner in which $CO_2$ lung concentrations are reduced as the steps of the method are carried out. Such a method is illustrated in FIG. 4. A subject may breath with reduced ventilation, typically characterized by reduced tidal volume and reduced frequency. This may occur naturally or as a result of mechanical ventilation and is often done to protect the lungs. The reduced ventilation reduces the amount of $CO_2$ ($VCO_2$) exhaled by the subject and increases the $CO_2$ concentration in the lung. This, in turn, reduces $CO_2$ gas exchange in the lung and increases end capillary blood $CO_2$ levels ($CcCO_2$). A data point produced from the $VCO_2$ and $CcCO_2$ measurements under these conditions is shown as point 100 in FIG. 4. To assist in the explanation, and for comparative purposes, FIG. 4 also shows the data of FIG. 1. Point 100 is analogous to an R value, i.e. is obtained under conditions of reduced gas transfer in the lungs.

To obtain the necessary alteration in lung $CO_2$ concentrations and gas transfer in the lungs required to produce another data point, the ventilation of the subject is increased, as by increasing the breathing tidal volume and/or respiration frequency. The increased ventilation, decreases lung $CO_2$ concentrations and increases $CO_2$ gas exchange in the lungs toward a more normal (N) condition. A data point produced from the $VCO_2$ and $CcCO_2$ measurements under these conditions is shown as point 102 in FIG. 4. The breathing of the subject may then revert to the former state.

The two data points are used in a regression analysis to produce line 104. In the example shown in FIG. 4, the slope of line 104 is the same as that of line 14, meaning that the functional cardiac output is the same for the two sets of conditions shown in FIG. 4. However, need not be, and usually will not be, the case. Line 104 intersects the abscissa of the graph of FIG. 4 at point 106. Due to the reduced $CO_2$ gas transfer in the lungs of the subject, as a result of the reduced ventilation of the subject, the end capillary blood $CO_2$ content ($CcCO_2$) at zero release of $CO_2$ from the blood of the subject indicated by point 106 will be higher than that indicated by point 16 in the example of FIG. 1. The venous blood $CO_2$ content ($CvCO_2$), also indicated by point 106, will similarly be higher. The venous blood $CO_2$ content so determined can be used in the Fick Equation 1 in the same manner as described above to determine the functional cardiac output.

The method of the present invention also allows venous blood $CO_2$ partial pressure ($PvCO_2$) to be accurately determined on a breath-by-breath basis. For each normal (N) breath taken by the subject, an new value for the end capillary blood $CO_2$ quantity, such as content ($CcCO_2$), will be determined. From this quantity, a new venous blood $CO_2$ content ($CvCO_2$) is determined in one of the ways described above. This new $CvCO_2$ value is then used to enter the graph of FIG. 2 along the ordinate. The new venous blood $CO_2$ partial pressure ($PvCO_2$) can be determined from the abscissa of the graph FIG. 2 knowing the amount of oxygen in the blood. The present invention thus also makes venous blood $CO_2$ partial pressure ($PvCO_2$) available on a breath-by-breath basis.

The foregoing determinations of the circulatory system condition of the subject, such as cardiac output or functional cardiac output, are in the nature of discrete measurements of the circulatory system condition at a particular point in time. In many cases, it is necessary, or desirable, to know whether a measurement made at one point in time remains an accurate indication of the condition of the subject at a subsequent point in time.

A further aspect of the present invention enables such a determination to be made without the need to determine complex compensation relationship factors. This aspect of the invention employs indicator variables that are directly or indirectly related to the monitored circulatory system condition value, such as cardiac output, functional cardiac output, or venous blood $CO_2$ partial pressure $PvCO_2$). For example, potentially useful indicators for conditions relating to blood flow are e.g. $CO_2$ elimination, end-tidal $CO_2$ concentration, and heart rate. For $PvCO_2$ such indicators may be end-tidal $CO_2$ and $CO_2$ elimination may be used.

To make a determination of whether a monitored condition value is still valid, initial values for the indicator variables are obtained that accurately reflect these variables at the time the monitored condition is measured with the discrete measurement. Preferably, this is carried out prior to or during the discrete measurement. The values so obtained serve in the nature of reference values. If the discrete measurement is made using the quantities in the Fick Equation 2, the $VCO_2^N$ and $FetCO_2^N$ may be recorded as reference values. Heart rate may also be recorded.

Once any disturbance, if present, in the $CO_2$ elimination due to $CO_2$ enrichment is passed, which may take 1–5 minutes, additional measurements of one or more indicator variables are obtained from the subject. As long as the values of the indicator variable remain unchanged, the discrete measurement of the monitored condition is still valid in describing the condition of the subject. Should any of the indicator variables change beyond a trigger level, which can be e.g. 10% or 20% of the initial or reference value, suitable action may be taken. This action may be an automatic initiation of a new discrete measurement, an indication to the user of the change and/or the direction of change in the monitored condition for further, user initiated, action, or an alarm that a change in the status of the subject has occurred.

By obtaining the subsequent measurements of the indicator variables on a breath-by-breath or heart beat-by-heart beat basis, with the method of the present invention, the validity of the discrete measurement of the circulatory system condition can be examined on such a basis and the validity of the discretely measured monitored condition value so extended to a time after the discrete measurement.

The direction of change in the measured condition value can be interpreted from the direction of change in the indicator variable value. For example, increases in $VCO_2$, $F_{ET}CO_2$, or in heart rate indicate that the cardiac output of the subject has increased over the discretely measured value, and vice versa.

It is recognized that some indicator variable changes may occur that are not the result of a change in the circulatory system condition of the subject. For example, an increase in ventilation of the subject would ordinarily cause the end tidal $CO_2$ concentration to decrease. Compensation to an affected indicator variable may be provided for such changes by determining changes in ventilation characteristics, such as, minute volume, tidal volume, and respiratory rate, and altering the indicator variable accordingly.

Figure 5:
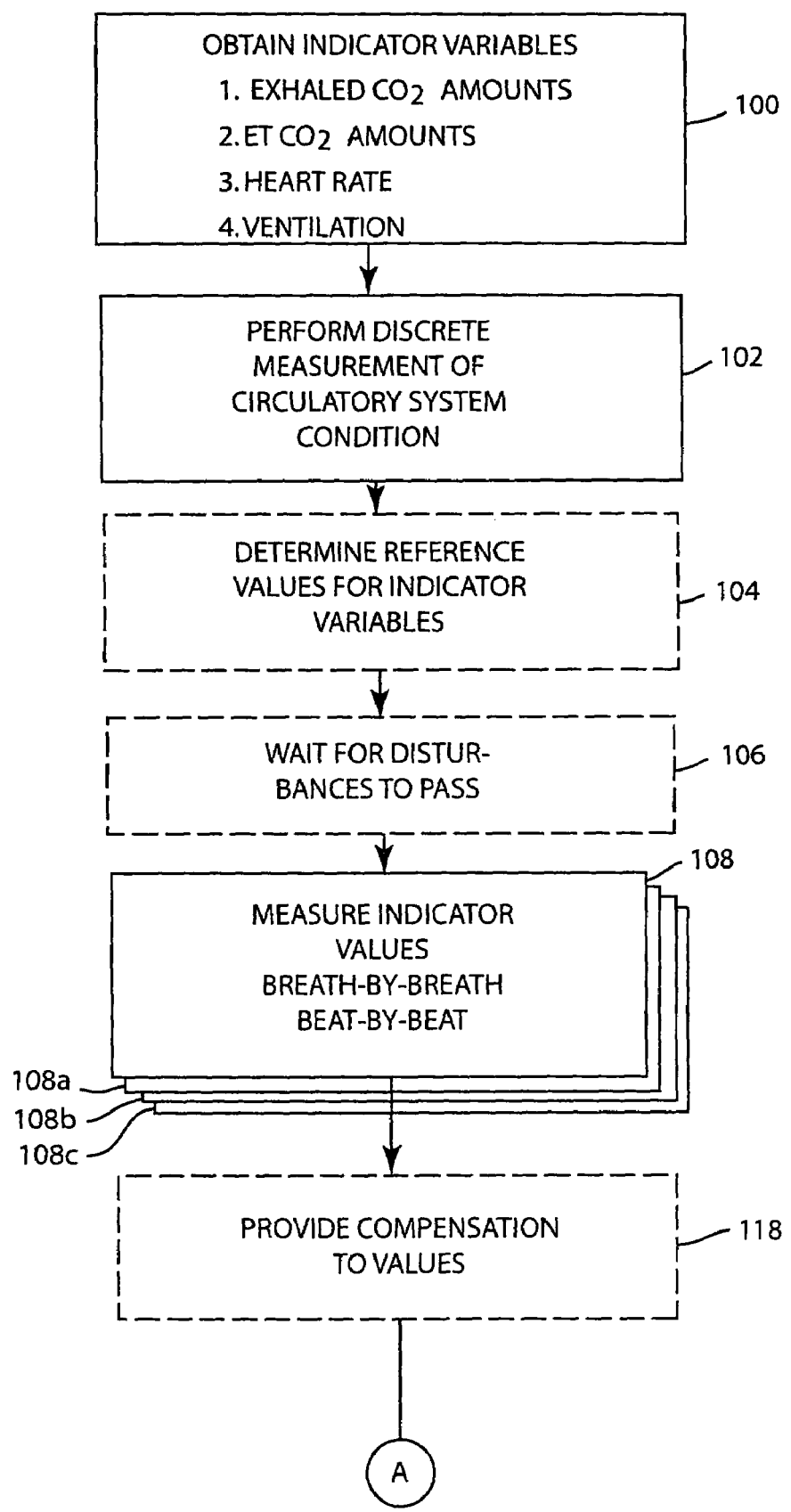

The steps of the method are shown in the flow chart of FIGS. 5 and 5A. The steps may be carried in, or under the direction of, calculation and control unit 70 shown in FIG. 3. In step 100, initial values are obtained for one or more indicator variables directly or indirectly related to the discretely measured circulatory system condition value. The determination of the indicator variable values may be obtained separately or in conjunction with performing a discrete measurement of the circulatory system condition in step 102.

To measure functional cardiac output this discrete determination may be non-invasive measurements of the type described above.

To measure cardiac output, this discrete determination may be a dilution measurement using thermodilution or dye dilution. In this technique, a bolus of marker is injected through a catheter into the bloodstream of the subject The catheter is fitted to sense the marker, either cold in thermodilution or color in dye dilution when the injected bolus is passing the sensor. The cardiac output is then determinated from the marker concentration response from the injection. Typically this method is used to measure the flow in pulmonary artery.

Before or after the discrete measurement is carried out, the obtained indicator variable values may be confirmed as valid reference values in step 104.

Once any disturbances created in the circulatory system condition of the subject in the course of making the discrete measurement have subsided, as at 106, one or more of the indicator variables are re-measured in step 108. As noted above, this can be carried out on a breath-by-breath or beat-by-beat basis, 108a, 108b, 108c,etc.

The subsequently obtained values are compared to the reference values in steps 110 and 112. If there is no difference between the two values, or if the difference is below a predetermined trigger level, the circulatory system condition value obtained from the previous discrete measurement is presumed still valid, as shown at 114.

If a difference is detected that is in excess of a trigger level, some action may be initiated by calculation and control unit 70, as at step 116. As noted above, these actions may include initiating a new discrete measurement, giving an indication of the change and/or direction of change in the circulatory system condition of the subject, as in readout device 80, or providing a warning or an alarm.

Compensation may be provided to the indicator variable values subsequently obtained in step 108 for changes in the value that do not reflect changes in circulatory system conditions in the subject. For example, the ventilation of the subject can be measured and changes in ventilation used to appropriately compensate an indicator variable, such as end tidal $CO_2$, as in step 118.

It is recognized that other equivalents, alternatives, and modifications aside from those expressly stated, are possible and within the scope of the appended claims.

The invention claimed is:

1. A method for non-invasively determining a condition of the circulatory system of a subject, the subject inhaling and exhaling breathing gases during breathing, said method comprising the steps of:
(a) measuring the amount of $CO_2$ in the breathing gases exhaled by the subject and the $CO_2$ concentration of the breathing gases exhaled by the subject for a first (1) breathing condition of the subject;
(b) determining at least one value of the amount of $CO_2$ released from the circulatory system of the subject ($VCO_2^1$) using the amount of $CO_2$ in the breathing gases exhaled when the subject is in the first condition;
(c) determining at least one value for a quantity indicative of the end capillary blood $CO_2$ content of the subject using the $CO_2$ concentration of the breathing gases exhaled when the subject in the first condition;
(d) altering the $CO_2$ concentration in the lungs of the subject;
(e) measuring the amount of $CO_2$ in the breathing gases exhaled by the subject and the $CO_2$ concentration of the breathing gases exhaled by the subject for at least one breath of the subject under a second (2) breathing condition of altered $CO_2$ in the lungs of the subject;
(f) determining at least one value for the amount of $CO_2$ released from the circulatory system of the subject ($VCO_2^2$), the determination of the value being carried out in a time period less than that required for blood leaving the lungs of the subject to pass through the circulatory system of the subject and return to the lungs, the determination of the value using the amount of $CO_2$ in the exhaled breathing gases for the second breathing condition;
(g) determining at least one value for a quantity indicative of the end capillary blood $CO_2$ content of the subject, the determination of the value being carried out in a time period less than that required for blood leaving the lungs of the subject to pass through the circulatory system of the subject and return to the lungs, the determination of the value using the $CO_2$ concentration of the breathing gases exhaled for the second breathing condition;
(h) performing a regression analysis using the determined $VCO_2^1$, $VCO_2^2$, and end capillary blood $CO_2$ quantity values to establish a regression line;
(i) extrapolating the regression line to obtain a value for the end capillary blood $CO_2$ quantity when the amount of $CO_2$ released from the circulatory system of the subject ($VCO_2$) is zero;
determining a further value for the quantity indicative of the end capillary blood $CO_2$ content for breathing of the subject in the first breathing condition;
forming a relationship between the value for the quantity indicative of the end capillary blood $CO_2$ content for breathing in the first breathing condition used in the regression analysis and the value obtained by extrapolating the regression line in step (i); and
applying the relationship to the further determined value for a quantity indicative of the end capillary blood $CO_2$ content to provide a new value for the value which was obtained by the extrapolation of the regression line in step (i).

2. The method according to claim 1 wherein steps (a) and (e) are further defined as measuring end tidal $CO_2$ concentrations of the breathing gases exhaled by the subject.

3. The method according to claim 2 further defined in that the quantity, for which values are determined in steps (c) and (g), comprises the end tidal $CO_2$ concentration of the exhaled breathing gases and that the value obtained in step (i) is the end tidal $CO_2$ concentration when the amount of $CO_2$ released from the circulatory system of the subject ($VCO_2$) is zero.

4. The method according to claim 3 further including the step of using the value obtained in step (i) to determine the functional cardiac output (FCO) of the subject using a non-differential form of the Fick equation.

5. The method according to claim 1 further defined in that the quantity, for which the values are determined in steps (c) and (g), comprises the $CO_2$ partial pressure in the blood of the subject and that the value obtained in step (i) is the $CO_2$ partial pressure of the end capillary blood of the subject when the amount of $CO_2$ released from the circulatory system of the subject ($VCO_2$) is zero.

6. The method according to claim 5 further including the step of using the value obtained in step (i) to determine the functional cardiac output (FCO) of the subject using a non-differential form of the Fick equation.

7. The method according to claim 1 or 2 further defined in that the quantity, for which the values are determined in steps (c) and (g), comprises the $CO_2$ content of the end capillary blood ($CcCO_2$) of the subject and that the value obtained in step (i) is the $CO_2$ content of the end capillary blood of the subject when the amount of $CO_2$ released from the circulatory system of the subject ($VCO_2$) is zero, which value comprises the $CO_2$ content of venous blood ($CvCO_2$).

8. The method according to claim 7 further defined as including the steps of:
determining the amount of oxygen in the venous blood of the subject; and
altering the obtained value for the venous blood $CO_2$ content ($CvCO_2$) in accordance with the amount of oxygen in the blood to provide a $CO_2$ partial pressure value ($PvCO_2$) for venous blood.

9. The method according to claim 8 wherein the step of the determining the amount of oxygen in the venous blood is further defined as determining the degree of oxygen saturation of the venous blood.

10. The method according to claim 8 further defined as including the steps of:
determining a further value for the quantity indicative of the end capillary blood $CO_2$ content for breathing of the subject in the first breathing condition;
forming a relationship between the value for the quantity indicative of the end capillary blood $CO_2$ content for breathing in the first breathing condition used in the regression analysis and the $CvCO_2$ value obtained by extrapolating the regression line in step (i);
applying the relationship to the further determined value for a quantity indicative of the end capillary blood $CO_2$ content to provide a new $CvCO_2$ value; and
altering the new $CvCO_2$ value in accordance with the amount of oxygen in the blood to provide a new $CO_2$ partial pressure value ($PvCO_2$) for venous blood.

11. The method according to claim 10 further defined as forming a relationship comprising a ratio.

12. The method according to claim 10 further defined as forming a relationship comprising a difference.

13. The method according to claim 8 further defined as carrying out the method on a breath-by-breath basis.

14. The method according to claim 7 further including the step of using the value obtained in step (i) to determine the functional cardiac output (FCO) of the subject using a non-differential form of the Fick equation.

15. The method according to claim 1 further including the step of using the value obtained in step (i) to determine the functional cardiac output (FCO) of the subject using a non-differential form of the Fick equation.

16. The method according to claim 1 further defined as including the steps of:
    determining further values for the amount of $CO_2$ released from the circulatory system of the subject ($VCO_2$) and for the quantity indicative of the end capillary blood $CO_2$ content for breathing of the subject in the first breathing condition; and
    using the value provided by the extrapolation of the regression line in step (i) and a further determined released $CO_2$ amount ($VCO_2$) and value for the quantity indicative of end capillary blood $CO_2$ content to determine the functional cardiac output of the subject using a non-differential form of the Fick equation.

17. The method according to claim 16 further defined as being carried out on a breath-by-breath basis.

18. The method according to claim 1 further defined as forming a relationship comprising as a ratio.

19. The method according to claim 1 further defined as forming a relationship comprising a difference.

20. The method according to claim 1 further including the steps of:
    determining further values for the amount of $CO_2$ released from the circulatory system of the subject ($VCO_2^N$) for breathing of the subject in the first breathing condition; and
    using the further determined released $CO_2$ amount ($VCO_2^1$), the further determined value for a quantity indicative of the end capillary blood $CO_2$ content, and the new value for the value which was obtained by extrapolation of the regression line in a non-differential form of the Fick equation to determine the functional cardiac output (FCO) of the subject.

21. The method according to claim 1 further defined as being carried out on a breath-by-breath basis.

22. The method according to claim 1 wherein the step of altering the $CO_2$ concentration in the lungs of the subject is further defined as increasing the $CO_2$ concentration in the lungs of the subject to reduce $CO_2$ gas exchange in the lungs of the subject.

23. The method according to claim 22 wherein the step of increasing the $CO_2$ concentration in the lungs of the subject is further defined as increasing the $CO_2$ content of the breathing gases inhaled by the subject.

24. The method according to claim 23 further defined as administering a bolus of $CO_2$ into the breathing gas inhaled by the subject.

25. The method according to claim 23 further defined as causing the subject to inhale breathing gas previously exhaled by the subject.

26. The method according to claim 23 wherein step (d) is further defined as increasing the $CO_2$ by an amount which improves the accuracy of the determination while avoiding undue build up of $CO_2$ in the blood of the subject.

27. The method according to claim 1 wherein the step of altering the $CO_2$ concentration in the lungs of the subject is further defined as decreasing the $CO_2$ concentration in the lungs of the subject to increase $CO_2$ gas exchange in the lungs of the subject.

28. The method according to claim 27 wherein the step of decreasing the $CO_2$ concentration in the lungs of the subject is further defined as increasing the ventilation of the subject.

29. The method according to claim 1 further defined as performing linear regression analysis using the $VCO_2^1$, $VCO_2^2$, and values for the quantity indicative of the end capillary blood $CO_2$ content of the subject determined using the exhaled breathing gas $CO_2$ concentrations for the first and second conditions.

30. The method according to claim 1 where the breathing gases supplied to the subject comprise air.

31. The method according to claim 1 further including the step of allowing the subject to take a sufficient number of breaths to stabilize the $CO_2$ content and $CO_2$ concentration of the exhaled breathing gases before taking the breathing measurements for the first breathing condition of the subject.

32. The method according to claim 1 further defined as determining a plurality of values for at least one of the amount of $CO_2$ released from the circulatory system of the subject ($VCO_2$) and the quantity indicative of the end capillary blood $CO_2$ content for use in performing the regression analysis.

33. The method according to claim 1 wherein steps (b) and (f) are further defined as determining at least one value of the amount of $CO_2$ released from the circulatory system of the subject ($VCO_2$) using the $CO_2$ content of the inhaled and exhaled breathing gases.

34. A method for determining a change in a measured condition of the circulatory system of a subject, said method comprising the steps of:
    (a) non-invasively obtaining, from the subject, an initial value for at least one selected variable comprising at least one of exhaled $CO_2$ amount, end tidal $CO_2$ amount, heart rate, and the amount of $CO_2$ released from the circulatory system of the subject ($VCO_2$);
    (b) carrying out a discrete measurement of a circulatory system condition of a subject;
    (c) obtaining a further value for the at least one selected variable subsequent to carrying out the discrete measurement;
    (d) comparing the further value of the variable with the initial value of said variable to determine whether the obtained variable has changed in value; and
    (e) initiating a carrying out of a further discrete measurement of a circulatory system condition of the subject responsive to a change in the value of the variable.

35. The method according to claim 34 further defined compensating the values of the selected variable for changes in the condition of the subject not arising from circulatory system conditions.

36. The method according to claim 35 further defined as compensating a selected variable for changes in ventilation of the subject.

37. The method according to claim 34 wherein the discrete measurement of circulatory system condition in steps (b) and (e) is carried out using a non-differential form of the Fick Equation and the quantities expressed therein and the circulatory system condition is the functional cardiac output (FCO).

38. The method according to claim 34 wherein the discrete measurement of circulatory system condition in steps (b) and (e) is carried out using a differential form of the Fick Equation and the quantities expressed therein.

39. The method according to claim 38 wherein the at least one selected variable further comprises at least one of the amount of $CO_2$ released from the circulatory system of the subject ($VCO_2$) and the end tidal $CO_2$ amount for normal conditions of the subject.

40. The method according to claim 38 wherein the measured circulatory system condition is functional cardiac output (FCO).

41. The method according to claim 34 wherein the discrete measurements of circulatory system condition are carried out using the quantifies expressed in a differential form of the Fick Equation and the circulatory system condition is venous blood partial $CO_2$ pressure ($PvCO_2$).

42. The method according to claim 40 wherein the at least one selected variable further comprises at least one of the amount of CO2 released from the circulatory system of the subject (VCO2) and end tidal CO2 for normal conditions of the subject.

43. The method according to claim 34 wherein the discrete measurement of the circulatory system condition in step (b) is carried out using a blood dilution technique.

44. The method according to claim 43 wherein the blood dilution technique uses a marker dye.

45. The method according to claim 43 wherein the blood dilution technique uses thermodilution.

46. The method according to claim 43 wherein the circulatory system condition measured is cardiac output (CO).

47. The method according to claim 34 wherein step (c) is further defined as sequentially obtaining further values of the at least one variable for comparison with the initial value.

48. The method according to claim 47 further defined as obtaining further values on a breath-by-breath basis.

49. The method according to claim 47 further defined as obtaining further values on a heart beat by heart beat basis.

50. The method according to claim 34 further defined as allowing disturbances caused by the carrying out of the discrete measurement to subside before obtaining a further value for said at least one selected variable.

51. The method according to claim 38 further defined as allowing disturbances caused by the carrying out of the discrete measurement to subside before obtaining a further value for said at least one variable.

52. The method according to claim 34 wherein step (d) is further defined as determining whether the variable has changed by a predetermined amount.

53. The method according to claim 34 further defined as providing an indication that a change in the value of the variable has occurred.

54. The method according to claim 34 further defined as providing an indication of the amount by which the value of the variable has changed.

55. The method according to claim 34 further defined as providing an indication of the direction in which a change in the value of the variable has occurred.

56. The method according to claim 34 further defined as providing an alarm.

57. Apparatus for determining a change in a measured condition of the circulatory system of a subject, said apparatus comprising:
    (a) means for non-invasively obtaining, from the subject, an initial value and subsequent value for at least one selected selected variable comprising at least one of exhaled $CO_2$ amount, end tidal $CO_2$ amount, heart rate, and the amount of $CO_2$ released from the circulatory system of the subject ($VCO_2$);
    (b) means for carrying out a discrete measurement of a circulatory system condition of a subject;
    (c) means for comparing the subsequent value of the variable with the initial value of said variable to determine whether the obtained variable has changed in value and for causing said means for carrying out a discrete measurement to carry out a further discrete measurement of a circulatory system condition of the subject responsive to a change in the value of the variable.

58. The apparatus according to claim 57 further defined as including means for compensating the values of the selected variable for changes in the condition of the subject not arising from circulatory system conditions.

59. The apparatus according to claim 57 wherein the measured circulatory system condition is functional cardiac output (FCO).

60. The apparatus according to claim 57 wherein the measured circulatory system condition is venous blood partial $CO_2$ pressure ($PvCO_2$).

61. The apparatus according to claim 57 wherein the measured circulatory system condition is cardiac output.

62. The apparatus according to claim 57 wherein the circulatory system condition is measured non-invasively.

63. The apparatus according to claim 57 wherein the circulatory system condition is measured invasively.

* * * * *